(12) United States Patent
Schneider et al.

(10) Patent No.: US 6,258,378 B1
(45) Date of Patent: *Jul. 10, 2001

(54) DELIVERY OF BIOLOGICALLY ACTIVE SUBSTANCE TO TARGET SITES IN THE BODY OF PATIENTS

(75) Inventors: Michel Schneider, Troinex; Feng Yan, Carouge, both of (CH); Agnés Hiver, Clarafond (FR)

(73) Assignee: Bracco Research S.A., Plan-les-Ouates (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,787

(22) Filed: Feb. 3, 1999

(30) Foreign Application Priority Data

Sep. 2, 1998 (EP) .................................................. 98810095

(51) Int. Cl.[7] ..................................................... A61K 9/127
(52) U.S. Cl. .................... 424/450; 424/1.21; 424/9.321; 424/9.51; 424/812; 436/829
(58) Field of Search .................. 424/450, 1.21, 424/9.321, 9.51, 812; 436/829

(56) References Cited

U.S. PATENT DOCUMENTS 5,445,813 * 8/1995 Schneider ............................ 424/9.51
5,580,575   12/1996 Unger et al. .
5,656,211    8/1997 Unger et al. .
5,773,024    6/1998 Unger et al. .

FOREIGN PATENT DOCUMENTS

WO 94/28873  12/1994 (WO) .
WO 94/28874  12/1994 (WO) .
WO 95/007072  3/1995 (WO) .

* cited by examiner

Primary Examiner—Gollamudi S. Kishore
(74) Attorney, Agent, or Firm—Nixon & Vanderhye P.C.

(57) ABSTRACT

The invention concerns a method for administering bioactive substances to patients at selected sites in the body and remotely promoting delivery of said media to selected organs or tissues in the body. The method comprises providing an administrable formulation comprising, dispersed in an aqueous carrier liquid, liposomes filled with bioactive substances and gas-filled microspheres, injecting said formulation into the circulation of a patient so that it is directed to a site of interest, and applying ultrasound pulses to said site so as to make the gas-filled microbodies explode and the gas confined therein to expand in the carrier liquid, the energy of expansion of said confined gas causing the liposome vesicles to open and release the trapped substances at said site. Also disclosed are formulations for delivery of biologically active substances to selected target sites in the organism, the formulations comprising an aqueous suspension of gas-filled microvesicles and liposomes filled with active susbstances such as drugs or diagnostic agents. The formulations are available in a kit form in which the kit comprises sterile precursor components.

15 Claims, No Drawings

DELIVERY OF BIOLOGICALLY ACTIVE SUBSTANCE TO TARGET SITES IN THE BODY OF PATIENTS

FIELD OF THE INVENTION

The present invention concerns a method and compositions or formulations for administering and controllably delivering bioactive substances or media to selected sites, e.g. organs or tissues, in the body of patients. The formulations comprise ingestible or injectable aqueous suspension of liposomes bearing active substances such as drugs or diagnostic agents encapsulated therein. The formulation is also available in kit form, the kits comprising sterile precursor components.

BACKGROUND ART

The targeted delivery via the circulation of liposomes encapsulating bioactive media like therapeutic or diagnostic substances towards selected areas in the organism combined with the assisted release of said substances at specific sites is attracting much attention in the medical field. For instance, N. Shoucheng et al., Int. J. Radiat. Oncol. Biol. Phys. 29 (1994), 827–834 have 25 disclosed injecting long lived liposomes (stealth) containing doxorubicine into the circulation of experimental animals and thereafter inducing controlled release of the doxorubicine at selected sites in the body via local hyperthermia induced by focused ultrasonic energy. Similarly, Bednarski et al. Radiology 204 (1997), 263–268 have disclosed the magnetic resonance guided targeting of liposome vesicles incorporating pharmaceuticals towards specific areas in the body, this being followed by the ultrasound controlled release into tissues of said pharmaceuticals, the effect being due to hyperthermialysis of the liposomal membrane.

In WO94/28873 and WO96/39079, there is disclosed a technique in which injectable targeted gas-filled microspheres, for instance gas-filled liposomes, comprising therapeutics embedded within the liposome bilayer membrane wall are directed to specific organs where they are caused to explode by ultrasonic irradiation in order to release said embedded therapeutic substances. It is difficult to incorporate drug into the gas filled liposomes (i.e. in the gas-phase or the surface membrane) without affecting their stability. If even a drug can be load in this kind of vesicles, it must be of a hydrophobic nature and the payload should be very low. Thus this method shows very limited practical utility. And also because after explosion, the therapeutic substance may stick some time to the constituents of the broken liposome membrane in which they were embedded, or the splintered parts of the liposome membranes may be simply "washed away" by the blood stream so that the active substance may not be released on the targeted site but elsewhere.

WO93/25241 discloses an ultrasound imaging technique in which a suspension of microspheres is targeted to organs of the body and caused to collapse under stimulation by ultrasonic energy, whereby a broad-band acoustic signal pulse is emitted and echo-detected by colour Doppler systems.

Although the techniques of the art have merit, a problem may arise due to the level of energy required to break the membrane of the liposomes and release the content thereof to a targeted area; if the area is located deep down in the body, the penetration of the energy beam into the body can have damaging effects to the intervening tissues. Hence searches have been undertaken to find a non-invasive energy releasing agent, closely associated with the liposome vesicles, which can innocuously help breaking the liposome membrane and release the trapped content thereof. In other words, it is strongly desired to make available an agent containing sufficient potential energy stored therein to open the liposome vesicles without harming the nearby or intervening tissues, said energy being liberated at will by external triggering means, so that the liposome encapsulated bioactive media be set free at a chosen site. The effect sought can be compared to that of a hypothetic prearmed spring to be remotely triggered and whose energy when released will cause the liposome content to be discharged at will. The present invention is set out to achieve this desired effect.

SUMMARY OF THE INVENTION

In brief, the method of the invention involves directing drug containing liposomes to selected areas in the organism and subsequently breaking or opening the liposomes to release the encapsulated content at a given site. In this method, the potential energy-containing agent to be used in association with the liposome vesicles and whose energy can be liberated at will to assist releasing the liposome encapsulated content consists of microparticles (microbodies) with confined air or gas. The microparticles are preferably air- or gas-filled microspheres, micro-vesicles, or microcapsules, more preferably air- or gas-filled microbubbles or microballoons. When air or gas-filled microspheres in close vicinity to liposome vesicles are caused to break or explode, the liberated cavitation energy will spread around and assist in opening the liposome membrane to free the encapsulated content or by changing the membrane permeability to enhance the drug diffusion. The triggering pulses of, for instance, radio or sound energy to burst the microspheres or microcapsules filled with the confined gas need not be as energetic as those required for directly acting on the liposomes membrane, hence the impact on nearby tissues is reduced.

The method of the invention is implemented via injectable compositions or formulations comprising liposomes (optionally targeted towards specific sites or organs) carrying encapsulated therein therapeutically or diagnostically useful agents and air or gas filled microspheres, i.e. microbubbles or microballoons which, optionally, may be associated with the liposomes. The microbubbles or microballoons are those disclosed in EP-A-0 474 833; EP-A-0 458 745; EP-A-0 502 814; EP-A-0 554 213; EP-A-0 619 743 and EP-A-0 682 530, all incorporated herein by reference.

The invention also includes precursor systems or kits which may include suspensions of liposomes encapsulating bioactive substances and suspensions of air- or gas-containing microspheres (stable microbubbles or microballoons), or dried liposomes having bioactive substances encapsulated therein in stabilised powder form, as well as suspensions in a carrier liquid of air- or gas-containing stable microbubbles or microballoons, or dried liposomes having bioactive substances encapsulated therein and microballoons in dry powder form, or microbubble precursors as pulverulent laminarized phospholipids stored in contact with air or a physiologically acceptable gas.

DETAILED DESCRIPTION OF THE INVENTION

The main aspects of the invention as set out in the accompanying claims are based on an unexpected finding that extremely efficient targeted delivery of biologically active ingredients may be achieved via a method in which an injectable composition comprising (a) liposomes containing encapsulated therapeutically or diagnostically useful agents and (b) air or gas filled microspheres, i.e. microbubbles or microballoons is administered to a patient. The injected formulation is allowed to reach via the circulation a selected/desired organ or tissue and then the targeted organ or tissues is irradiated with an energy beam (preferably ultrasonic) to burst or cause burst of the gas or air-filled microspheres, the released gas energy thereby opening the adjacent liposomes vesicles, thus causing dispense of the encapsulated biologically active substance(s) at the desired site in the organism of the patient.

Upon administration of an effective amount of such formulation into the vascular or the lymphatic systems of said patient, the progression in the circulation of the administered formulation toward the selected site may be monitored by ultrasonic or MRI imaging means, so that the irradiation and consecutive burst of the gas filled microspheres by sonolysis or otherwise is effected only when the formulation reaches or passes over or through the desired site. Clearly, the process of irradiation may be carried out continuously or intermittently during each cyclic circulation of the formulation through or by the targeted site.

The ultrasonic irradiation may be carried out by a modified echography probe adapted to simultaneously monitor the reflected echo signal and thereby provide an image of the irradiated site. This may further improve efficacy of the method.

Obviously, the total amount of energy discharged at the organ site may not need to exceed that required to break the gas-filled microspheres for and release the bioactive substance, thus minimizing irradiation of the tissue at the targeted organ or site. The frequency of the ultrasonic irradiation required to break the microspheres may vary from about 0.3 to 3 MHz. It should be noted that although any blood or lymph perfused tissue may be targeted according to the invention, it is believed that the most efficiently treated affections relate to endothelial lesions, macrophages around tumours, tumour vascular tissues, thrombosis, etc.

As universally admitted, liposome solutions are aqueous suspensions of microscopic, spherically shaped, vesicles whose core may hold entrapped aqueous solutions of substances dissolved in the liposome carrier liquid. These vesicles are usually formed of one or more concentrically arranged molecular double layers (lamellae) of amphipatic compounds, i.e. compounds having a lipophobic hydrophilic moiety directed toward the water phase) and a lipophilic hydrophobic moiety holding the layers together. (See for instance "Liposome Methodology", Ed. L. D. Leserman et al, Inserm 136, May 2–8 1982). Bioactive substances can be encapsulated within the aqueous phase of the core of liposome vesicles and the suspensions can be injected into the body, whereby they can be made to circulate in the blood or the lymph; as said before, release of the encapsulated substances will then result from the opening or rupture or collapse of the liposomal vesicle membrane. The targeted method is particularly suitable for local administration of toxic substances which, if not targeted, could (and would) otherwise cause significant secondary effects to other organs; such drugs include for instance Amphotericin B or NSAID's or drugs whose administration is required over prolonged periods such as Dexamethasone, insulin, vitamin E, etc. The method is also suitable for administration of thrombolytic agents such as urokinase or streptokinase, or antitumoral compounds such as Taxol etc.

Definitions of the terms "microbubbles" and "microballoons" as used herein are given in the above-referenced publications. For instance, in the present disclosure "microbubble" specifically designates air or gas filled microspheres in suspension in a liquid carrier phase which generally result from the introduction therein of air or a gas in divided form, the liquid phase preferably also containing surfactants or tensides to control the surface properties thereof and the stability of the bubbles. In the microbubbles, the boundary or envelope around the gas core is mostly evanescent and may simply consists of the gas/liquid interface layer which is generally only a few nanometer thick. The term of "microballoon" designates preferably air or gas microspheres with a tangible material boundary or envelope formed of molecules other than that of the liquid of suspension, for instance, a protein or a polymeric or lipidic membrane, this shell being tens or hundreds of nm thick.

More specifically in the present invention, one will consider that the internal volume of the microbubbles is limited by the gas/liquid interface, or in other words, the microbubbles are only bounded by an envelope involving the molecules of the liquid and surfactants loosely bound at the gas to liquid interface or boundary. In the present invention, the surfactants preferably comprise one or more phospholipids at least in part in laminar or lamellar form. The term "lamellar form" indicates that the surfactants are in the form of thin films involving one or more molecular layers ("laminate" form). Converting such film forming phospholipid surfactants into lamellar form can easily be done by liposome methodology, for instance by pressure homogenisation or by sonication under acoustical or ultrasonic frequencies. In this connection, it should be remembered that, as said above, the liposome vesicles membrane itself is made of phospholipids in lamellar form.

Many surfactants or tensides, including lipids, particularly phospholipids, can be laminarized to correspond to this kind of structure. In this invention, one preferably uses the lipids commonly used for making liposomes, for instance saturated phospholipids, natural or preferably synthetic, as well as other surfactants or glycerides which can be made into layers or films.

Particularly preferred are the phospholipids selected from neutral phospholipids such as hydrogenated phosphatidyl choline (HSPC), dipalmitoyl-, distearoyl- and diarachidoyl phosphatidylcholine (DPPC, DSPC, DAPC); negatively charged phospholipids such as dipalmitoyl and distearoyl phosphatidic acid (DPPA, DSPA), dipalmitoyl and distearoyl phosphatidylserine (DPPS, DSPS), dipalmitoyl and distearoyl phosphatidylglycerol (DPPG, DSPG); reactive phospholipids such as phosphatidyl ethanolamine derivatives coupled to a polyethylenglycol, a biotinyl, a glutaryl, a caproyl or a succinyl amine.

The microballoons which are useful in this invention are described in EP-A-0 458 745. They have a tangible envelope made of substantive material, e.g. a polymeric membrane with definite mechanical strength. In other terms, they are microspheres of flexible solid material in which the air or gas is more or less tightly confined. Microballoons made by sonication of viscous protein solutions like 5% serum albumin and having diameters in the 1–20 $\mu$m range, and stabilised by denaturation of the membrane forming protein may also be used.

The polymer which constitutes the envelope or bounding membrane of the injectable microballoons preferred in this invention can be made from most hydrophilic, biodegradable physiologically compatible polymers. Among such polymers, which may be natural or synthetic, one can cite polysaccharides of low water solubility, polycyanoacrylates, polylactides and polyglycolides and their copolymers, copolymers of lactides and lactones such as γ-caprolactone, δ-valerolactone, polypeptides, and proteins such as gelatin, collagen, globulins and albumins. The great versatility in the selection of synthetic polymers is another advantage of the present invention since, as with allergic patients, one may preferably avoid using microballoons made of natural proteins (albumin, hemoglobin) like in U.S. Pat. No. 4,276,885 or EP-A-0 324 938. Other suitable polymers include poly-(ortho)esters (see for instance U.S. Pat. Nos. 4,093,709; 4,131,648; 4,138,344; 4,180,646); polylactic and polyglycolic acid and their copolymers, for instance DEXON (J. Heller, Biomaterials 1 (1980), 51; poly(DL-lactide-co-γ-caprolactone), poly(DL-lactide-co-δ-valerolactone), poly-(DL-lactide-co-γ-butyrolactone), polyalkylcyanoacrylates; polyamides, polyhydroxybutyrate; polydioxanone; poly-β-aminoketones (Polymer 23 (1982), 1693); polyphosphazenes (Science 193 (1976), 1214); and polyanhydrides. References on biodegradable polymers can be found in R. Langer et al., *Macromol. Chem. Phys.* C23 (1983), 61-126. Polyamino acids such as polyglutamic and polyaspartic acids can also be used as well as their derivatives, i.e. partial esters with lower alcohols or glycols. One useful example of such polymers is poly-(t.butyl-glutamate). Copolymers with other amino acids such as methionine, leucine, valine, proline, glycine, alanine, etc. are also possible. Other derivatives of polyglutamic and polyaspartic acid with controlled biodegradability have been reported (see WO 87/03891; U.S. Pat. No. 4,888,398 and EP-A-0 130 935) all incorporated herein by reference.

The gases to fill the microspheres of this invention include air, and most gases common in the field of echogenic gases, for instance $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$, air, oxygen, nitrogen, carbon dioxide, noble gases, and mixtures thereof. Innocuous, low boiling liquids which will vaporise at body temperature or by the action of remotely applied energy pulses, like $C_6F_{14}$, are also usable as a volatile confinable microparticle component in the present invention.

The confined gases may be at atmospheric pressure or under pressures higher or lower than atmospheric; for instance, the confined gases may be at pressures equal to the hydrostatic pressure of the carrier liquid holding the liposomes and the gas filled microspheres.

In the present invention, the gas-filled microspheres may be more or less closely associated with the liposomes, i.e. they may simply be admixed with the liposome vesicles whereby they will statistically distance from each other. Alternatively, the liposome vesicles and the gas-filled microspheres can be organised to have affinity for each other, for instance they may each be provided with the molecular components of a conjugate pair. As an example, an antigen may be incorporated in the liposome membrane and an antibody in the microspheres, or vice-versa, so that antigen-antibody conjugation will cause the microspheres and the liposome vesicles to couple with each other. Other coupling systems involving donors and receptors in the classes of substances listed below are also possible: amphetamines, barbiturates, sulphonamides, monoamine oxydase inhibitor substrates, hormones, enzymes, lipids, ligands specific of cellular membranes, antihypertensive agents, neurotransmitters, aminoacids, oligopeptides, radio-sensitizers, steroids (e.g. estrogen and estradiol), mono- and polyclonal antibodies as well as fragments thereof, carbohydrates (such as glucose derivatives), fatty acids, muscarine receptors and substrates (such as 3-quinuclidinyle benzilate), dopamine receptors and substrates (such as spiperone), biotin, peptides and proteins capable of binding specific receptors, benzodiazepine receptors and substrates.

Systems involving multiple coupling sites are also possible. For instance, in a particular embodiment of the present invention's method and formulation, the envelopes of both liposome vesicles and gas microspheres are provided with biotin coupling sites and a suspension thereof in an aqueous carrier liquid is admixed with avidin, whereby both the liposome vesicles and gas microspheres will coalesce together by coupling with avidin.

The liposomes used in this invention are preferably of the long-lived (stealth) type, i.e. resistant to capture by the RES. Stealth liposomes are disclosed in documents such as *J. Pharmacy & Pharmacol.* 39 (1987), 52P); EP-A-0 354 855, WO 91/05545; EP-A-0 759 785; EP-A-0 731 690; *Biochimica et Biophysica Acta* 1126 (1992), 255–260, and "Stealth Liposomes" Edited by D. Lasic and F. Martin (1995) CRC Press, London, all publications incorporated herein by reference.

Particularly preferred embodiments of the present invention involve liposomes which comprise three components: A. a neutral lipid, for example, a nonionic or zwitterionic lipid or their derivatives; B. a negatively or positively charged lipid, and C. a lipid bearing a functional component, for example N-biotinyl-PE or PEG-PE. Cholesterol or cholesterol derivatives can be used to replace a part of component A, as generally known to the skilled person.

The lipids used to make the liposomes can be selected from a group comprising: lipids and phospholipids such as soy lecithin, partially refined lecithin, hydrogenated phospholipids, lysophosphate, phopshpatidylcholine, phosphatidylethanolamine, phosphatidylserine, phosphatidylinositol, cardiolipin, sphingolipids, gangliosides, cerebrosides, ceramides, other esters analogue of phopshpatidylcholine (PAF, lysoPAF); synthetic phospholipids such as L-α-lecithin (dilauroylphosphatidylcholine, dipalmitoylphosphatidylcholine, dilinoloylphosphatidylcholine, distearoylphosphatidylcholine, diarachidoylphosphatidylcholine); phosphatidylethanolamine derivatives, such as 1,2-diacyl-sn-glycero-3-phosphoethanolamine, 1-acyl-2-acyl-sn-glycero-3-phosphoetanolamine, dinitrophenyl- and dinitrophenylamino caproylphosphatidylethanolamine, 1,2-diacyl-sn-glycero-3-phosphoethanolamine-N-polyethylene glycol (PEG-PE), N-biotinyl-PE, N-caproylamine PE, N-dodecylamine-PE, N-MPB-PE, N-PDD-PE, N-succinyl-PE, N-glutaryl-PE; phosphatidyl glicerols such as dipalmitoylphosphatidylglicerol, distearoylphosphatidylglicerol; phosphatidic acids (1,2-diacyl-sn-glycero-3-phosphate salt, 1-acyl-2-acyl-sn-glycero-3-phosphate sodium salt; phosphatidylserine such as 1,2-diacyl-sn-glycero-3-[phospho-L-serine] sodium salt, 1-acyl-2-acyl-sn-glycero-3-[phospho-L-serine] sodium salt, lysophosphatidic acid; cationic lipids such as 1,2-diacyl-3-trimethylammoniumpropane (TAP), 1,2-diacyl-3-dimethylammoniumpropane (DAP), N-[1-(2,3-dioleoyloxy)propyl]-N,N',N''-trimethylammonium chloride (DOTMA); polymerizable lipids such as diyne PC, diynePE for example 1,2-bis(10,12-tricosadiynoyl-sn-glycero-3-phosphocoline; phospholipids with multivarious headgroups such as phosphatidylethanol, phosphatidylpropanol and phosphatidylbutanol, phosphatidylethanolamine-N-monomethyl, 1,2-disteraoyl(dibromo)-sn-glycero-3-phosphocoline; phospholipids with partially or fully fluorinated fatty acid chains.

Emulsifiyng or surfactant agent may also be incorporated in the liposomes or used for liposome preparation, such as Pluronics®, Poloxamer®, Span®, Brig®, Tweens®, Triton-X®; fluorinated surfactants such as Zonyl®.

For preparing the liposome suspensions useful in the present invention, one can apply the conventional techniques in the field, for instance that disclosed in the aforesaid documents and the following one: Liposomes as Drug Carriers by G. Gregoriadis, Wiley & Sons, New-York (1988).

For instance, as disclosed in GB-A-2,134,869, microspheres (10 µm or less) of a hydrosoluble carrier solid (NaCl, sucrose, lactose and other carbohydrates) are coated with a phospholipid mixture; then, by dissolution of this coated carrier in an aqueous phase, one will obtain liposomic vesicles. In GB-A-2,135,647 insoluble particles, e.g. glass or resin microbeads are coated by moistening in a solution of lipids in an organic solvent followed by removal of the solvent by evaporation. The lipid-coated microbeads are thereafter contacted with an aqueous carrier phase, whereby liposomic vesicles will form in that carrier phase.

It is of particular interest to note that in the present invention, the generation of the microbubbles, the eventual burst of which will help split the liposome vesicles membrane and liberate the encapsulated content, is directly (although partly) related the formation of the liposomes. Indeed, as disclosed in EP-A-0 474 833, admission of air or a gas in a suspension of liposomes will provide stable microbubble suspensions containing from about $10^7$ to $10^{10}$ microbubbles/ml, or more. Also, according to the same document, similar bubble suspensions will result from exposing for a time to air or a gas formulations of dried laminar phospholipids (which can be compared to liposomes stored dry), and thereafter admixing with a carrier liquid. Hence, it is of interest in the present invention (although not compulsory) to start with liposomes suspensions or solutions prepared by any known technique, and thereafter introduce air or a gas, whereby a stable suspension of microbubbles will form stabilised by the presence of the surfactants in lamellar form. Of course, the material making the liposome walls shall have to be modified within the scope of the present invention, i.e., for instance by admixing therewith or covalently grafting thereon foreign molecules designed for coupling as described before. Alternatively, one may also start with "unloaded" liposome vesicles, i.e. vesicles not having yet a bioactive substance encapsulated therein. Then, before or after air or a gas is introduced into the liposome solution to provide a desired suspension of microbubbles, loading of the liposome vesicles can be effected as disclosed in EP-A-0 514 523.

In an embodiment, a dry powder formulation of liposomes containing bioactive media encapsulated therein can be prepared according to document U.S. Pat. No. 4,229,360, the liposome wall-forming material containing an agonist coupling precursor (e.g. biotin). Then, the liposome suspension is regenerated using an aqueous carrier liquid containing an antagonist (e.g. avidin), whereby bubbles will form together with the liposome vesicles, both stabilized by the biotin-containing lipids and coupling via the avidin in the solution.

In a variant, the liposome preparations and the gas-filled microsphere formulations can of course be prepared individually and admixed together before administration. They may also be administered individually in which case the administration is effected sequentially in any order with or without delay between the injections i.e. to delay interference of the microbubbles and the liposome vesicles. In certain applications or modes of treatment several injections of microbubbles may be envisaged to assist release of the liposome content at several sites or for repeated release of the liposome active ingredient at the same site.

As said before, microballoons with confined air or gas are also usable according to the invention to help opening liposome vesicles. In this case, the microballoons are prepared separately from the liposomes, preferably according to the techniques disclosed in EP-A-0 458 745, and thereafter admixed with the suspension of liposomes of interest. Naturally also, the envelope of the microballoons will preferably contain a coupling precursor designed to eventually conjugate with a receptor of the liposome membrane (or vice-versa). Practical achievements of such an embodiment are disclosed in the experimental part hereafter.

In order to implement the method of the invention, one will administer the preparations according to usual routes, e.g. intravenous, perfusion, etc. for instance, one can inject into the circulation of subjects by usual means (IV or otherwise) targeted (or non-targeted) preparations as described above containing in admixture liposomes with trapped bioactive media and microspheres (microbubbles or microballoons) with confined air or gas therein. After a time, when the injected material has reached a targeted organ or tissue site in the body, energy pulses are applied from the outside (for instance above or on the skin in relation with the site) to cause the gas containing particles to explode; the cavitation energy thus released by the explosion brings about the opening of the liposome envelope and the discharge of the encapsulated materials.

Energy pulses required to explode the gas-filled microspheres are preferably sonic or ultrasonic pulses. In this connection see the publication by M. W. Miller et al. in *Ultrasound in Med. & Biol.* 22 (1996), 1131–1154. In broad, transducer systems can be applied directly to the body or through a water-path couplant with the frequencies in the range from about 0.3 to 3 MHz. In a preferred embodiment, there is used a modified ultrasound probe for monitoring displacement of the bubbles after administration and the destruction thereof when appropriate at the application site. The collapsing of the bubbles is then depicted by a dramatic change of the reflected echo signal. The monitoring signal is in the range of 1 MHz to 10 MHz and preferably between 2 and 7 MHz.

In view of the various formulation embodiments to be possibly used in the present invention, systems of precursors developed comprise components to be admixed before use and delivered commercially for instance in a kit form for easier storage and shipping. These precursor systems may include the following embodiments:

(A) Solution (or suspensions) of liposomes having bioactive substances encapsulated therein. The solution is then treated with air or a gas, for instance infused before application by means of a syringe or otherwise.

(B) Solution (or suspensions) of liposomes having bioactive substances encapsulated therein and a suspension of air- or gas-containing microspheres (stable microbubbles or microballoon) to be admixed therewith.

(C) The kit which comprises dried liposomes having bioactive substances encapsulated therein in stabilised powder form and a suspension in a carrier liquid of air- or gas-containing microbubbles or microballoons. Both components are to be admixed before use.

(D) The kit which may comprise dried liposomes having bioactive substances encapsulated therein in stabilised powder form, microballoons in dry powder form, or microbubble precursors as pulverulent laminarized phospholipids stored in contact with air or a gas and an administrable carrier liquid, said components to be admixed before use.

(E) In a simplified variant, the kit may comprise dried liposomes stored in stabilised powder form in contact with air or a gas and having bioactive substances encapsulated therein and an administrable carrier liquid, which may be admixed before use, whereby a stable suspension of microbubbles is form due to the stabilising effect of the phospholipids.

As already mentioned, the method of the invention based on microbubble burst acoustic cavitation can be used not only to promote liposome lysis for drug delivery and contrast enhancement in ultrasound imaging, but also to modify cell permeability for gene transfection or expression. The liposomes may be thermo-sensitive, fusogenic, pH-sensitive, stealth (e.g. PE-PEG) with or without specific homing factors and loaded with different therapeutic, imaging or genetic substances. Preferably, the liposomes are unilamellar, a structure, which enables high drug encapsulation capacity (i.e. high active substance/lipid ratio), and a low shear stability under acoustic cavitation.

The following Examples further illustrate the invention.

Example 1

A) Biotin-labeled LUV (Large Unilamellar Vesicles) Liposomes

There were dissolved in 150 ml of a mixture (1:2) of chlorofom and methanol at 50° C. 0,75 g of hydrogenated soy phosphatidyl choline (HSPC, from Nattermann Chemie, Germany), 50 mg of dipalmitoylphosphatidic acid (DPPA, from Sygena, Switzerland), and 10 mg of N-biotinyl Cap-PE (Avanti Polar Lipids, USA). To this were added 200 g of 1 mm glass beads (Polyscience Inc., USA) and the whole was homogenized in a homogenizer. After removing the solvent on the rotavapor, the residue was suspended in 200 ml of buffer solution (10 mM TRIS+0,9% NaCl, pH 7.2) containing 10% of optical tracer drug (carboxyfluorescein) and the mixture heated to 60° C. to hydrate the lipids. The beads were removed and the liposome solution extruded 5 times through 1 $\mu$m polycarbonate filter membranes; then the solution was dialyzed against the same buffer to eliminate untrapped substances. After dialysis, the solution was checked (Coulter counter), the mean diameter of the liposome vesicles being about 1.3 $\mu$m.

B) Biotin Labeled Microbubbles

In 150 ml of buffer (10 mM TRIS+0,9% NaCl, pH 7.2) were dispersed at 65° C. 200 mg of dipalmitoylphosphatidyl glycerol (DPPG) and 200 mg of distearoylphosphatidylcholine (DSPC), all from Sygena, 10 mg of N-biotinyl Cap-PE and 5 g of Pluronic® F-108. After cooling to room temperature, the solution was placed into an emulsifier apparatus equipped with a Polytron® head and emulsified (10,000 rpm) for 2 min under an atmosphere of perfluorobutane ($C_4F_{10}$) to provide a milky bubble suspension. The upper foam layer was discarded and the solution allowed to settle. The top layer of bubble suspension was collected and resuspended in TRIS-NaCl buffer; thereafter, the decantation operation was repeated twice, whereby the bubbles in the final purified suspension had a mean size of 2.6 $\mu$m at a concentration of $5 \times 10^8$ bubbles/ml.

C) Ultrasonic Release of Carboxyfluorescein (CF) from Liposomes

Three 205 $\mu$l different samples were prepared as follows:

a) 20 $\mu$l of liposome solution (A)+185 $\mu$l of TRIS-NaCl buffer b) 20 $\mu$l of liposome solution (A)+5 $\mu$l of TRIS-NaCl buffer+180 $\mu$l of microbubble solution (B)

c) 20 $\mu$l of liposome solution (A)+5 $\mu$l of avidin solution (1 mg/ml in TRIS buffer)+180 $\mu$l of microbubble solution (B).

The samples placed in Eppendorff tubes were subjected for 10 min to the effect of ultrasound in a Branson 5200 apparatus (47 KHz, 0.2 W/cm$^2$). After treatment, the samples were centrifuged and the fluorescence of the tracer released in the supernatant measured with a Kontron SFM-25 fluorimeter (excitation at 480 nm; emission at 520 nm). Identical samples (untreated) were used as control. The results are gathered in the Table below

TABLE 1

| | CF release (%) | |
|---|---|---|
| Sample | No ultrasound (control) | Ultrasound treated |
| a | 2.3 | 4.1 |
| b | 10 | 23.6 |
| c | 9.7 | 53.4 |

As seen from the foregoing results the maximal delivery of liposome entrapped substance occurs when the bubbles couple with the liposomes via conjugation with avidin.

Example 2

MLV liposomes (MLV=multilamellar vesicles) were prepared at the concentration of 10 mg (of mixture of lipids)/ml (of aqueous phase) using a 75:20:5 (w/w) mixture of DSPC/cholesterol/DPPA. The water phase was a 10 mM solution of CF in buffer. Hydration of the lipid mixture (liposome vesicles formation) was effected by heating to 65° C. under mild agitation for 10 min.

The samples to be tested were made of 100 $\mu$l of liposome suspension plus various quantities of the microbubbles preparation (B) disclosed in Example 1 (see the Table below). Then, for testing, the samples were further diluted to make 6 ml with TRIS buffer and circulated in a thin-wall plastic tubing (f=4 mm) immersed in a constant 37° C. bath with a peristaltic pump. Pulses from a 8550 Tabor generator, amplified with a A-150 ENI RF amplifier, were applied with a 1 MHz focused transducer (Panametric Inc., USA) placed at 9 cm from the tube. The acoustic pressure was measured in the tube with a hydrophone connected to a digital scope (DL-4100 from Yokogawa, Japan). The following further experimental parameters were applied: Pulse length, 10 $\mu$s; burst number, 100; pressure amplitude in the tube (peak to peak), 1.6 Mpa; exposure time, 3 min; flux rate 15 ml/min. The results are gathered in the next Table

TABLE 2

| Sample | CF release ($\mu$mol) |
|---|---|
| Liposomes only | 1.0 |
| +0.1 ml B (from Ex. 1) | 1.9 |
| +0.5 ml B | 7.7 |
| +2.5 ml B | 15.9 |

Example 3

A suspension of MLV liposomes was prepared as in Example 2. A portion thereof (LUV-1) was converted to LUV by repeated freeze and thaw, followed by five 1 μm membrane ex-trusions. Another portion (LUV-2) was further extruded through membranes of successively 0.6, 0.4 and 0.2 μm. The samples to be tested were admixed with the microbubble suspension (B) to produce a liposome/microbubble volume ratio of 1:5. The samples were tested for CF release as indicated in Example 1. The results are gathered in the next table.

TABLE 3

| Liposomes | Size (nm) | Encapsulation ratio (μl/mg) | CF release (%) |
|---|---|---|---|
| MLV | 810 | 2.3 | 16 |
| LUV-1 | 630 | 8.1 | 41 |
| LUV-2 | 260 | 1.3 | 10 |

Example 4

This example illustrates the influence of various parameters such as transducer frequency, output power, flow rate, exposure time, etc. on the gas microbubble-ultrasound induced liposome lysis.

Example 2 was repeated with a constant bubble/liposome concentrations and different ultrasound exposures. The results have shown that the change in tranducer frequency from 1 to 2.25 MHz lowers the degree of release of CF from liposomes under the condition where all other parameters were kept constant. Similar observation was made for changes in the flow rate. The higher the flow the lower is the number of the exploded or destroyed microbubbles.

It has been observed that the microbubble destruction was more efficient at higher acoustic powers having as a direct consequence higher release of CF from liposomes. Hence it may be said that the degree of liposome lysis was proportional to the increase in amplitude applied.

The effect of the exposure time was apparently dependent on different settings of power, frequency and flow rate. The liposome lysis was complete when all microbubbles in the suspension were destroyed. However, during a continuous infusion of the microbubbles, the total liposome lysis increased and remained high as long as the microbubble infusion was maintained.

Experimental results (3 min US irradiation, liposomes 500 μl, bubbles 2.5 ml):

| | Frequency variation at 1.5 MPa, 10 ml/min | | Acousitc pressure variation at 1 MHz and 10 ml/min | | Flow rate variation at 1 MHz and 1.5 MPa | | |
|---|---|---|---|---|---|---|---|
| | 1 MHz | 2.25 MHz | 0.5 MPa | 1.5 MPa | 5 ml | 10 ml | 15 ml |
| Bubble %* | 81.9 | 68.5 | 69.5 | 81.9 | 94.4 | 81.9 | 70.3 |
| Lysis %** | 18.7 | 5.1 | 7.3 | 18.7 | 25.3 | 18.7 | 13.2 |

*% of bubbles destroyed by US irradiation, determined by Coulter.
** Liposome lysis determined by CF release.

These data show that the lysis of liposomes relates closely to the amount of bubbles destroyed by ultrasound (sonolysis).

Example 5

Large unilamellar liposomes (LUV) were prepared according to M. H. Gaber et al., *Int. J. Rad. Oncol. Bio.* *Phys.* 36 [5] (1996), 1177–1187. A molar ratio mixture (100:50:30:6) of DPPC (dipalmitoylphosphatidyl choline), HSPC, cholesterol, and PE-PEG (distearoylphosphatidyl ethanolamine derivatized with polyethyleneglygol 1900) was dissolved in an organic solvent (see Example 1), and thereafter the obtained solution was allowed to evaporate in contact with a surface iso as to form a film of the phospholipids on that surface. Then a 10 mM solution of CF in TRIS (10 mM+0.9% NaCl, pH 7.4) was added in quantity required to form a 5 mg/ml solution of liposomes; hydration was effected by heating above the transition point and the liposome solution was extruded 5 times through membranes of decreasing pore size. The mean bubble size, measured by light scattering (Nycom apparatus) was about 140 nm.

Samples were prepared by admixing with the microbubble preparation of Example 1, this being also in the same proportion. Table 4 below shows the CF release after exposition of the samples to ultrasonic energy as in Example 1 for 10 min a various temperatures. The data also include controls (no bubbles, no ultrasound) as indicated. They clearly demonstrate the effect of temperature. Note also that in the absence of the "catalyzing" influence of the gas-containing microbodies, the effect of the ultrasound is not much over that of temperature.

TABLE 4

| | CF release (%) at t° C. | | |
|---|---|---|---|
| Sample | 25 | 37 | 41 |
| Heat only | 3 | 17 | 28 |
| Heat + US | 4 | 17 | 31 |
| Heat + US + bubbles | 16 | 32 | 54 |

Another aspect of using the cavitation energy liberated in a medium by the explosion of gas-filled microbodies is to act on the droplets of an emulsion of pharmaceutically acceptable liquids in a carrier phase. One can therefore convey the admixture of emulsion and microbubbles to a selected area in the body and when there, one will trigger the disruption of the droplets by the remote controlled disintegration of the bubbles, The liquid in the droplets can have bioactive substances dissolved therein which will then distribute in the area of interest. In a variant, if sufficiently low boiling, this liquid will simply vaporize and produce a plethora of new bubbles and enhanced echo signal. Many other aspects of using the localized supply of energy from exploding bubbles could be envisaged.

Example 6

1 g of dipalmitoyl phosphatidyl glycerol (DPPG, Sygena, Switzerland) and 10 mg of N-Biotinyl Cap-PE (Avanti Polar Lipids, USA) were dissolved in 100 ml of distilled water containing 3 grams of Pluronic®-F108 (a non-ionic surfactant). A clear solution was obtained at 60° C. under agitation. This solution was mixed with a gas (ex. $C_4F_{10}$) in a high speed homogenizer (Polytron®, 10, 000 rpm) for few minutes. An opaque suspension containing between $10^8$ and $10^9$ of gas microbubbles/ml with a size distribution between 0.7 and 20 μm was obtained. To remove the surfactant, the-free (non-incorporated) biotinyl molecules and narrow the microbubble size distribution, the suspensions were repeatedly decanted (washed) several times with water until all surfactant in the suspension was removed (this was controlled by the IR or HPLC). The size distribution and microbubble number may be equally tailored by controlling the duration of decantation and the volume of the supernatant phase recovered (bubble phase). Typically, three decantations were sufficient. In the case where the homing or biomolecules were unstable in aqueous solutions, the microbubble suspension were frozen (e.g. below -18° C.) and stored until use.

As the surfactants or detergents were used only to facilitate the lipid solubilization and gas microbubble formation, they were removed after the microbubble formation. All surfactants capable of dissolving, cosolubilising or dispersing the phospholipids in aqueous medium can be utilized. Examples of such surfactants are Pluronic®, Polaxmer®, Tween®, Spans®, Chaps (non-denaturing zwitterionic detergent often used for membrane biochemistry) and numerous hydrocarbon surfactants (sodium alkyl sulfate, etc.), fluorocarbon surfactants (e.g. perfluoro alkyl polyoxyethylene), ionic or non-ionic. As the principal element of the microbubble stabilising shell, many phospholipid molecules may be utilized (e.g. phosphatidyl choline, phosphatidyl serine, phosphatidyl glycerol, etc.), but for the method in this example the negatively charged phospholipids are preferred because of their co-solubility in water in the presence of other surfactants. Many perfluorocarbon containing synthetic lipids can also be used in this technique for microbubble preparation. Moreover, a mixture of more than two surfactants or of several lipid molecules can be used in this preparation, which gives often microbubbles with interesting properties and a high yield of microbubbles.

This example demonstrates that "surfactant or detergent depletion" method (similar to the process used in liposome preparation) may be employed to incorporate the homing factor into the microbubbles giving them specific properties for targeting in vivo.

What is claimed is:

1. A method of delivering a drug or diagnostic agent to a selected site in the body of a patient comprising the steps of:
   (i) injecting into the circulation of said patient an administrable formulation consisting essentially of, as a suspension in a carrier liquid, microballoons bounded by a solid polymeric membrane carrying an entrapped physiologically acceptable gas and liposome vesicles filled with a liquid containing said drug or diagnostic agent;
   (ii) allowing said formulation to reach the selected site through the circulation of said patient, and
   (iii) ultrasonically irradiating said site so as to cause the microballoons to explode and the entrapped gas to expand in the carrier liquid, the energy of expansion of said gas causing the liposome vesicles to open and release the drug or diagnostic agent at said site.

2. A method of delivering a drug or diagnostic agent to a selected site in the body of a patient comprising the steps of:
   (i) injecting into the circulation of said patient an administrable formulation consisting essentially of, as a suspension in a carrier liquid, microbubbles bounded by an evanescent gas/liquid interfacial closed surface and carrying an entrapped physiologically acceptable gas and liposome vesicles filled with a liquid containing said drug or diagnostic agent;
   (ii) allowing said formulation to reach the selected site through the circulation of said patient, and
   (iii) ultrasonically irradiating said site so as to cause the microbubbles to explode and the entrapped gas to expand in the carrier liquid, the energy of expansion of said gas causing the liposome vesicles to open and release the drug or diagnostic agent at said site.

3. The method of claim 1 or 2, wherein the microballoons or microbubbles are exploded by irradiation with ultrasonic pulses having frequencies of about 0.3 to 3 MHz.

4. The method of claim 3, wherein the ultrasonic pulses are provided by a standard or a modified echography probe adapted to simultaneously monitor the reflected echo signal and thereby provide an image of the irradiated site.

5. The method of claim 2, wherein the carrier liquid comprises amphipatic compounds to stabilize the gas-containing microbubbles against premature collapse.

6. The method of claim 5, wherein the amphipatic compounds are phospholipids.

7. The method of claim 6, wherein the phospholipids are saturated.

8. The method of claim 6, wherein the microbubbles are stabilized by a monolayer of phospholipids at the gas/liquid interface.

9. The method of claim 1, wherein the membrane of the microballoons is made from a natural or a synthetic polymer.

10. The formulation of claim 1 or 2, wherein the entrapped physiologically acceptable gas is selected from the group consisting of $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$, $C_6F_{14}$, air, oxygen, nitrogen, carbon dioxide, noble gases, and mixtures thereof.

11. The method of claim 6, wherein the phospholipids are neutral phospholipids selected from the group consisting of hydrogenated phosphatidyl, choline (HSPC), dipalmitoyl-, distearoyl- and diarachidoyl phosphatidylcholine (DPPC, DSPC, DAPC), negatively charged phospholipids selected from the group consisting of dipalmitoyl and distearoyl phosphatidic acid (DPPA), DSPA), dipalmitoyl and distearoyl phosphatidylserine (DPPS, DSPS), dipalmitoyl and distearoyl phosphatidylglycerol (DPPG, DSPG); reactive phospholipids selected from the group consisting of phosphatidyl ethanolamine derivatives coupled to a polyethyleneglycol, a biotinyl, a glutaryl, a caproyl or a succinyl amine.

12. The method of claim 1 or 2, wherein the liposome vesicles and the air or gas-filled microballoons or microbubbles have affinity for each other.

13. The method of claim 12, wherein the liposome vesicles and the microspheres are each provided with the respective components of a conjugate pair.

14. The method of claim 13, wherein an antigen is present in the liposome membrane and an antibody in the gas-filled component, or vice-versa, so that antigen-antibody conjugation will cause the liposome vesicles and the microballoons or microbubbles to be brought together.

15. The method of claim 12, wherein both the liposome vesicles and the microballoons or microbubbles are provided with a donor coupler element and the formulation further includes a multisite acceptor element, whereby donor and acceptor will become conjugated and the liposome vesicles and the microballoons or microbubbles are brought together.

* * * * *